United States Patent [19]

Griffin

[11] 4,243,048
[45] Jan. 6, 1981

[54] BIOPSY DEVICE

[75] Inventor: Lawrence C. Griffin, Toledo, Ohio

[73] Assignee: Jim Zegeer, Arlington, Va. ; a part interest

[21] Appl. No.: 725,300

[22] Filed: Sep. 21, 1976

Related U.S. Application Data

[63] Continuation of Ser. No. 168,415, Aug. 2, 1971, abandoned, which is a continuation of Ser. No. 857,858, Sep. 15, 1969, abandoned.

[51] Int. Cl.³ .............................................. A61B 17/36
[52] U.S. Cl. ..................... 128/751; 128/754; 128/305
[58] Field of Search ............... 128/2 R, 2 B, 305, 310, 128/311, 328, 303.14, 296, 346, 754, 751

[56] References Cited

U.S. PATENT DOCUMENTS

| | | | |
|---|---|---|---|
| 769,829 | 9/1904 | Mott | 128/311 |
| 1,167,014 | 1/1916 | O'Brien | 128/2 B |
| 1,867,624 | 7/1932 | Hoffman | 128/2 B |
| 2,505,358 | 4/1950 | Gusberg et al. | 128/2 B |
| 2,516,492 | 7/1950 | Turkel | 128/2 B |
| 2,816,552 | 12/1957 | Hoffman | 128/305 |
| 3,157,524 | 11/1964 | Artandi | 128/296 X |
| 3,394,699 | 7/1968 | Koett | 128/2 B |
| 3,404,677 | 10/1968 | Springer | 128/2 B |
| 3,473,533 | 10/1969 | Freda | 128/305 |
| 3,606,878 | 9/1971 | Kellogg, Jr. | 128/2 B |

FOREIGN PATENT DOCUMENTS

| | | | |
|---|---|---|---|
| 270419 | 5/1965 | Australia | 128/2 B |
| 1160573 | 1/1964 | Fed. Rep. of Germany | 128/2 B |
| 972731 | 10/1964 | United Kingdom | 128/346 |
| 125870 | 5/1969 | U.S.S.R. | 128/2 B |

*Primary Examiner*—Kyle L. Howell
*Attorney, Agent, or Firm*—Jim Zegeer

[57] ABSTRACT

A biopsy device for obtaining tissue specimens, particularly from endocervical canal. A cutting anvil, typically of a non-metallic material such as plastic, is carried at one end of an elongated shaft. An annular cutting blade, typically of a metallic material, on the end of a hollow shaft is telescoped on the shaft carrying the cutting anvil. The device includes a locking arrangement to lock the cutting edge of the device in engagement with the anvil during insertion of the device to the selected site and during removal of same from the body so that during insertion there is no inadvertent damage to tissue and, most importantly, no inadvertent loss and spreading of possibly diseased tissue and cells during removal. Further, the device includes an adjustment means whereby the size of the specimen may be selected prior to insertion in the patient.

2 Claims, 2 Drawing Figures

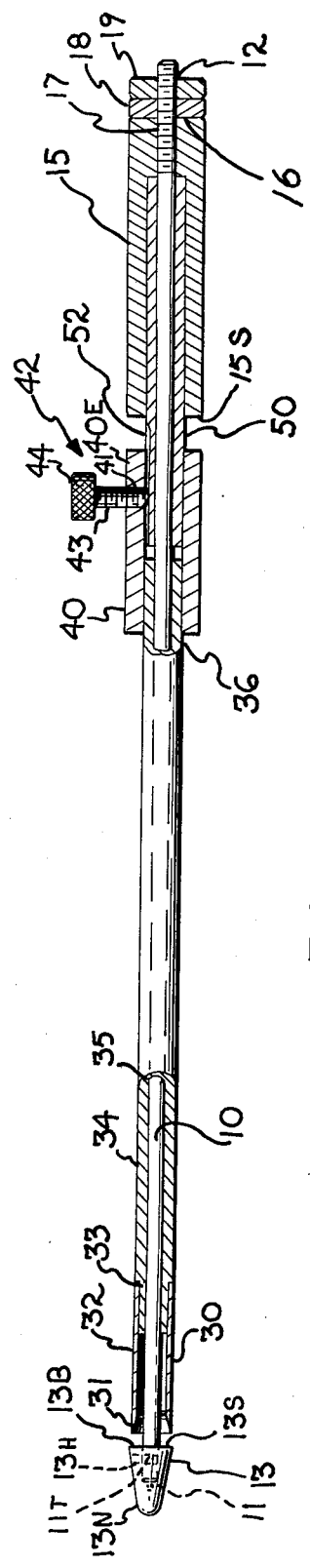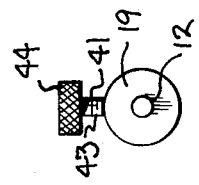
FIG. 1
FIG. 2

BIOPSY DEVICE

This is a continuation of application Ser. No. 168,415, filed Aug. 2, 1971 now abandoned which was a continuation of Ser. No. 857,858 filed Sept. 15, 1969 now abandoned.

PRIOR ART

U.S. Pat. No. 1,167,014
U.S. Pat. No. 1,867,624
U.S. Pat. No. 2,505,358

THE INVENTION

This invention is particularly related to devices for obtaining tissue specimens from the body which device is physically very small and which may be used in the manner of a catheter or the like, and which, by its small size and dimensional parameter and manner of operation permits obtaining of tissue specimens at internal body sites normally not available unless the site has been exposed by surgery or greatly dilated and enlarged for remedial action. A particularly important application of the invention is the essentially painless performance of endocervical biopsies of females.

In accordance with this invention, there is provided an elongated shaft carrying on the distal end thereof a non-metallic, plastic cutting anvil which also is shaped to provide a guiding protuberance for entrance to the patient's body, as for example, the endocervical canal of females. A hollow tubular member is telescopically fitted on the shaft and has an annular cutting element on the distal end thereof equal to slightly less than the diameter of the cutting anvil, and an enlarged internal diameter forming a chamber for receiving a specimen severed from a selected site. At the proximal end of the tubular member is a locking member for locking the tubular member to the shaft during entry and removal of the device from the patient. The proximal end of the shaft is provided with a micrometer adjustment in a handle portion so that the size of the specimen may be selected by the physician.

The above and other features of the invention will become more apparent from the following specification, taken with the accompanying drawing wherein:

FIG. 1 is a partial cross-sectional view of a biopsy device incorporating the invention, and FIG. 2 is an end-view thereof looking from the right hand end of FIG. 1.

With reference to FIG. 1, the device is shown as including a central metal shaft 10, the distal and proximal ends 11 and 12, respectively, being threaded. A non-metallic cutting anvil 13 has a partial bore 13B threaded to threadably engage the threaded distal end 11 of shaft 10. Cutting anvil 13 has a bullet shaped nose 13N.

Preferably, cutting anvil 13 is constructed out of a suitable non-metallic material such as a plastic or polymer. Although almost any of the well known polymeric construction materials can be selected such as nylon, polyvinyl chloride, polyolefins, etc., there is contemplated in one broad practice hereof the use of polymeric or like material which is not harmful to animal tissue; that is, a material which is inert or which does not react in a harmful way with animal tissue. In one highly preferred embodiment, there is used a material which will tend to decompose in the prolonged presence of animal tissue. Such a material is highly important where the cutting anvil 13 accidentally breaks off of the shaft 10 and becomes lodged in the animal tissue. If there is a non-harmful reaction of the tissue and the cutting anvil material of construction such that the latter will merely decompose in time, there will be no need for any fishing or like operation.

Typical of the type of materials contemplated include polyvinyl pyrollidone, hardened animal protein such as collagen, and water degradable polyurethanes and polyureas. Reference is also made to U.S. Pat. No. 3,434,846 and the class of materials disclosed therein.

Anvil surface 13S is planar and in a plane normal to the axis of central shaft 10. While the threaded engagement of the threaded distal end with the threaded bore 13B provides positive locking of anvil 13 to shaft 10, as an additional safety feature, there may be a transverse threaded bore 11T in distal end 11 and aligned with a hole or opening (dotted lines 13H) in anvil 13 through which a screw (not shown) may be passed to prevent any rotation of anvil 13 relative to central shaft 10.

Handle member 15 is provided with fine knurlations (not shown) on the exterior surface thereof and has an end wall 16 in which is formed threaded aperture or hole 17 which has the threaded proximal end 12 of central shaft 10 threadably engaged therewith. The threaded proximal end 12 projects beyond end wall 16 of handle 15 and threadably engaged with same are a pair of locking nuts 18 and 19, both of which are provided with surface knurlations (not shown) for permitting manual locking adjustment of same after the threaded proximal end of shaft 10 has been moved in or out to adjust the distance between the cutting anvil 10 and blade 30 and hence the size of the specimen to be removed.

Cutting blade 30 has an annular cutting edge 31 encompassing a cross-sectional area slightly less than the cross-sectional area of planar anvil surface 13S. While annular cutting edge 31 is in a plane substantially parallel to planar anvil surface 13S so that severance of the specimen is uniform and complete, a feature of the invention is that in the event all of cutting edge 31 is not substantially parallel to anvil surface 13S, it can be cut or scored by the annular cutting edge to assure complete and clean severance of the specimen so that on withdrawal of the device there is no pulling and tearing of tissue. Such operation is especially effective if the cutting anvil 13 is constructed out of a plastic material which can be conveniently cut or scored by the annular cutting edge 31.

Annular cutting blade 30 has an interior diameter somewhat larger than the diameter of central shaft 10 to thereby form a chamber 32 for retention of any specimen. Moreover, blade 30 is threadably secured to the distal end 33 of tubular shaft 34 so that it may be removed for sharpening, replacement or disassembly of the entire device for cleaning. Tubular shaft 34 is slidingly telescoped over central shaft 10, the walls of bore 35 thereof being in sliding engagement with the surfaces of shaft 10 to aid in maintaining cutting edge 31 in a plane normal to the axis thereof and substantially parallel to the planar surface 13S of anvil 13.

A tubular member 40 is secured to the end 36 of tubular shaft 34 remote from cutting blade 30 and has an extension 40E extending beyond the end 36. (It will be appreciated that tubular shaft 34 and tubular member 40 may be machined or formed as an integral member, if desired, and that other components may likewise be formed as integral components.) End 40E has a threaded bore 41 which threadably receives the threaded shaft 43 of locking screw 42. Locking screw 42 has a knurled head or knob 44.

Tubular member 50, which may be formed integrally with handle member 15, extends beyond handle member 15 and has a diameter substantially equal to the diameter of tubular shaft end 36 so that it is encompassed by end 40E of tubular member 40, at least with respect to where the shaft of locking screw 42 projects through the internal wall surface of member 40. A groove 52 may be formed in the exterior surfaces of member 50 if desired. Engagement of the ends of locking screw 42 with the surface of tubular member 50 locks or secures the cutting blade 30 in engagement with anvil 13 (or at any position between a fully opened position and a fully closed position, as where only scrapping of tissue is desired). It will be appreciated that since central shaft 10 is movable relative to tubular member 50, the blade carrying tubular shaft member 34 may be locked with end 40E of member 40 in abutment with shoulder 15S on handle 15 and the distance between anvil surface 15 and cutting edge 31 adjusted by extending proximal end 12 of shaft 10 more or less outwardly and then locking same in position by means of locking nuts 18 and 19. However, it will be appreciated that the locking of the cutter blade 31 can be achieved by engagement of locking screw 42 directly on the surface of shaft 10 in which case the adjustment of the size of specimen cannot be achieved with blade 31 locked.

What is claimed is:

1. A surgical device for extracting a biopsy specimen from the endocervical canal of females without surgery or dilation and enlargement thereof, comprising an elongated shaft, a rounded plastic member shaped as a guiding protuberance for entrance to the endocervical canal of a female, said plastic member being secured to the end of said elongated shaft, a hollow metallic tubular blade member telescopically fitted on said shaft for sliding and rotary motion along and about the longitudinal axis of said elongated shaft, an annular cutting element on the end of said tubular blade member, said hollow blade member having an internal diameter which is larger than the external diameter of said elongated shaft so as to form a specimen receiving chamber, said guiding protuberance having a planar trailing surface which can be cut or scored by said annular cutting element to assure complete and clean severance of the specimen so that on withdrawal of the device from the endocervical canal of the female there is no pulling and tearing of tissue and no inadvertent spreading of possibly diseased tissue and cells during removal of the said device from the endocervical canal, and wherein said plastic member is constituted by a material which will tend to decompose in the prolonged presence of animal tissue.

2. The invention as defined in claim 1 wherein said material which will tend to decompose in the prolonged presence of animal tissue is selected from the group including polyvinyl pyrollidone, hardened animal protein such as collagen and water degradeable polyurethanes and polyureas.

* * * * *